United States Patent
Muller et al.

(10) Patent No.: US 6,481,423 B2
(45) Date of Patent: Nov. 19, 2002

(54) DYNAMIC EGR CONCENTRATION ESTIMATION METHOD FOR A MOTOR VEHICLE ENGINE

(75) Inventors: Martin Muller, Ann Arbor, MI (US); Peter M. Olin, Ann Arbor, MI (US); Bart Hubert Schreurs, Athus (BE)

(73) Assignee: Delphi Technologies, Inc., Troy, MI (US)

( * ) Notice: Subject to any disclaimer, the term of this patent is extended or adjusted under 35 U.S.C. 154(b) by 56 days.

(21) Appl. No.: 09/732,658

(22) Filed: Dec. 1, 2000

(65) Prior Publication Data

US 2002/0066442 A1 Jun. 6, 2002

Related U.S. Application Data

(60) Provisional application No. 60/239,852, filed on Oct. 12, 2000.

(51) Int. Cl.⁷ .............................................. F02M 25/07
(52) U.S. Cl. .................................. 123/568.11; 73/30.03; 73/117.3
(58) Field of Search .......... 123/568.11, 568.21–568.27; 701/103, 108; 73/30.03, 117.3

(56) References Cited

U.S. PATENT DOCUMENTS 5,273,019 A * 12/1993 Matthews et al. ...... 123/406.48
6,247,462 B1 * 6/2001 Wild et al. ............. 123/568.21

* cited by examiner

*Primary Examiner*—Gene Mancene
*Assistant Examiner*—Arnold Castro
(74) *Attorney, Agent, or Firm*—Vincent A. Cichosz

(57) ABSTRACT

An improved method of dynamically estimating the concentration of recirculated exhaust gases in air/fuel mixture of an internal combustion engine equipped with an exhaust gas recirculation (EGR) system. The EGR concentration at engine intake ports is separately estimated with static and dynamic models, and the EGR concentration for control purposes is determined by adjusting the result of the dynamic model based on a deviation of the dynamic model from the static model. This method provides the total EGR concentration, but can alternatively provide the inert EGR concentration through the inclusion of an exhaust inert ratio model.

12 Claims, 2 Drawing Sheets

DYNAMIC EGR CONCENTRATION ESTIMATION METHOD FOR A MOTOR VEHICLE ENGINE

CROSS REFERENCE TO RELATED APPLICATION

This application claims the benefit of U.S. Provisional Patent Application No. 60/239,852 filed on Oct. 12, 2000 the disclosure of which is incorporated by reference herein in its entirety.

TECHNICAL FIELD

This invention relates to a method of accurately and dynamically estimating the concentration of recirculated exhaust gases in the gas entering the combustion chamber of an internal combustion engine equipped with an exhaust gas recirculation (EGR) system.

BACKGROUND OF THE INVENTION

Recirculation of a controlled amount of exhaust gas into the intake air stream of an internal combustion engine, via EGR valve control and/or valve overlap control, has been effectively utilized for improving exhaust gas emissions and fuel economy. Specifically, the recirculated exhaust gas tends to reduce the peak combustion temperature and pressure, which in turn, reduces nitrogen oxide components (NOx) in the exhaust. Fuel economy improvements occur because the recirculated exhaust gases raise the intake manifold pressure, reducing engine pumping losses. On the other hand, reduced combustion stability and degraded engine performance can occur if the EGR concentration is too high. Thus, it is necessary to have a reliable estimation of the EGR concentration of the gas entering the combustion chamber if the advantages of EGR are to be fully realized without also incurring the disadvantages. Steady state estimations of the EGR concentration can be readily obtained, but what is needed is a continuously reliable estimation of the EGR concentration. The need is especially great in direct injection gasoline engines where the controller initiates large changes in EGR concentration when changing combustion modes.

SUMMARY OF THE INVENTION

The present invention is directed to an improved method of dynamically estimating the concentration of recirculated exhaust gases entering the combustion chambers of an internal combustion engine equipped with an exhaust gas recirculation (EGR) system. According to the invention, the EGR concentration at the engine intake ports is separately estimated based on a dynamic model of air and exhaust gas mixing in the engine, and the EGR concentration for control purposes is determined by adjusting the result of the dynamic model based its deviation from an estimate of the EGR concentration based on a conventional steady-state model. This method provides the total EGR concentration, but can alternatively provide the inert EGR concentration through the inclusion of an exhaust inert ratio model.

DESCRIPTION OF THE PREFERRED EMBODIMENT

Figure 1:
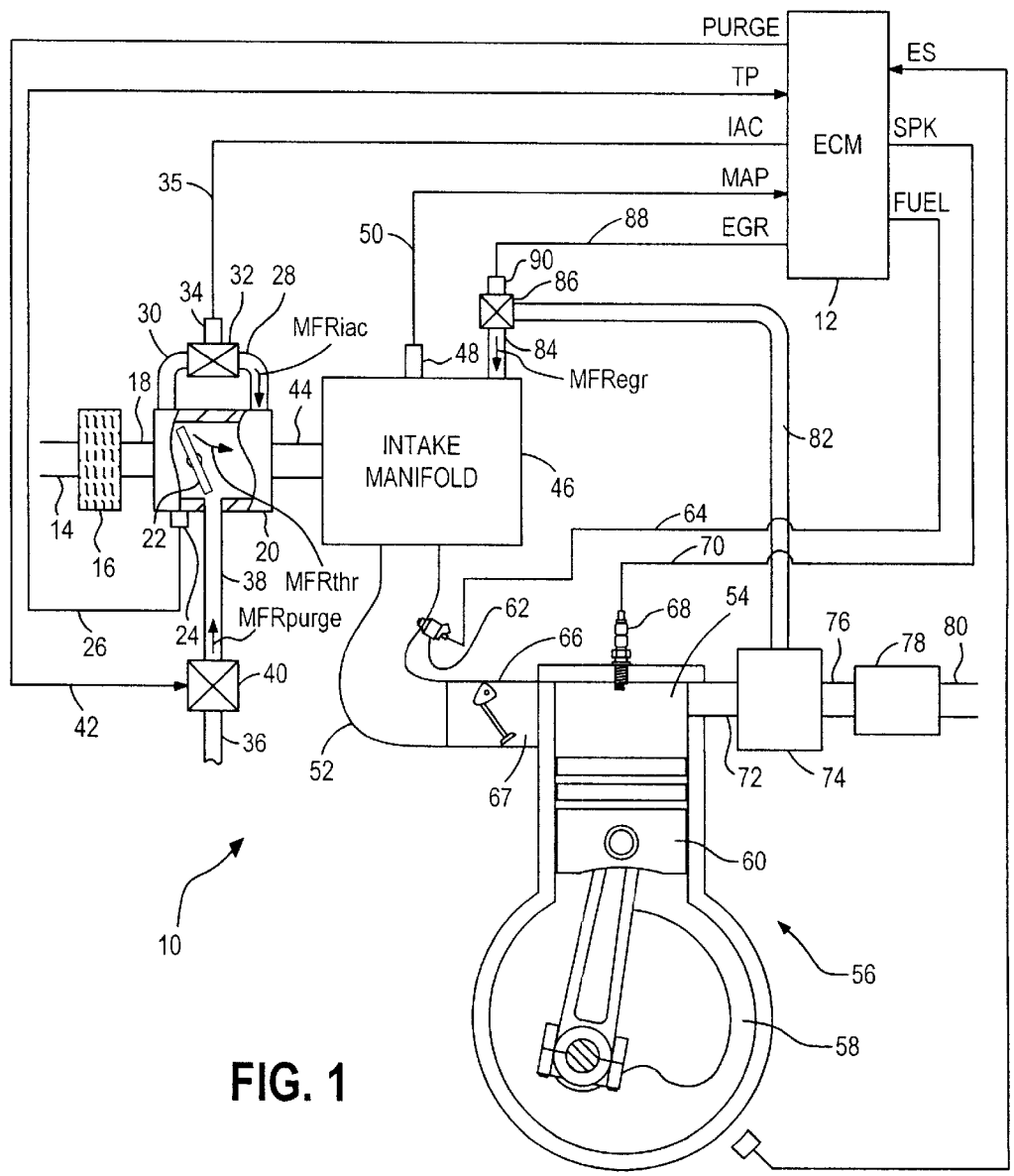
FIG. 1 is a schematic diagram of an internal combustion engine equipped with an exhaust gas recirculation system and a microprocessor-based engine control module programmed to carry out the method of this invention.

Referring to the drawings, and particularly to FIG. 1, the reference numeral 10 generally designates a four-stroke internal combustion engine controlled by a microprocessor-based engine control module (ECM) 12. Inlet air at atmospheric pressure passes through fresh air inlet 14, air cleaner 16 and intake duct 18 into throttle body 20. A throttle plate 22 rotatably disposed in the throttle body 20 is manually or electronically positioned to vary restriction to the inlet air. The position of throttle plate 22 is detected by the sensor 24, which provides a throttle position signal (TP) to ECM 12 on line 26. A portion of inlet air is routed past throttle plate 22 through conduits 28 and 30 and a conventional idle air bypass valve 32. The bypass valve 32 is positioned by a stepper motor 34, and the ECM 12 supplies an idle air control (IAC) signal on line 35 to stepper motor 34 during engine idle for purposes of maintaining a desired engine idle speed. Additionally, air and fuel vapors from the purge canister of the engine fuel system (not shown) are directed to the throttle body 20 via conduits 36 and 38, and the purge control valve 40. Purge control valve 40 is typically an on/off valve, and ECM 12 electrically controls its state with a purge signal (PURGE) on line 42.

Airflow out of throttle body 20 is coupled through intake duct 44 into the intake manifold plenum volume 46 (referred to hereinafter simply as the intake manifold). A conventional pressure transducer 48 is exposed to gas pressure in the intake manifold 46 and provides a manifold absolute pressure signal (MAP) to ECM 12 via line 50. Individual cylinder intake runners 52 couple intake manifold 46 to the combustion chambers 54 of respective engine cylinders 56, only one cylinder 56 being shown in FIG. 1. Each combustion chamber 54 is separated from the engine crankcase 58 by a respective piston 60 which engages the inside wall of the respective cylinder. A quantity of fuel is injected via conventional fuel injector 62 in response to a fuel injection command signal (FUEL) from ECM 12 on line 64. Although engine 10 is depicted as a port fuel injected engine with the fuel being injected into the intake runner 52, it will be recognized, as indicated above, that the method of the present invention is applicable to direct injection engines (gasoline or diesel) as well. In the illustrated embodiment, the fuel mixes with the inlet air and is drawn into the combustion chamber 54 during an intake event when intake valve 66 opens an intake port 67. The air-fuel mixture is ignited in the combustion chamber 54 during a combustion event initiated by a timed spark across the spaced electrodes of spark plug 68, which is controlled by ECM 12 via a spark control signal (SPK) line 70. Gasses produced during the combustion event are exhausted during an exhaust event through exhaust runner 72 to exhaust manifold 74. The exhaust gasses pass through the exhaust manifold 74 to an exhaust duct 76 leading to catalytic converter 78 and tailpipe 80.

Of particular relevance to the present invention, a portion of the exhaust gasses are drawn from exhaust manifold 74 through conduits 82, 84 and exhaust gas recirculation (EGR) valve 86 into the intake manifold 46 for mixing with inlet air for delivery to the cylinder combustion chambers 54. The ECM 12 issues an EGR control signal (EGR) on line 88 for positioning the EGR valve 86 with solenoid or stepper motor 90 to vary the dilution of the fresh inlet air with exhaust gasses for improved emission control and fuel economy.

As indicated above, it is important to have an accurate estimate of the EGR concentration in the gas entering the engine combustion chambers 54 in order to take full advantage of the benefits of EGR without incurring the disadvantages that occur when the EGR concentration is too high. Additionally, an accurate estimate of the EGR concentration is needed for accurate control and estimation of the air/fuel ratio of the mixture entering the combustion chambers 54.

In general, conventional control strategies utilize a steady-state model to estimate the steady-state concentration (SS%EGR) of recycled exhaust gas in the intake manifold gas flow. According to the steady-state model, SS%EGR is estimated as the ratio of the EGR mass flow rate into intake manifold 46 (MFRegr) to the total engine intake manifold gas flow rate (MFRtot). That is:

$$SS\%EGR = MFRegr/MFRtot \tag{1}$$

For this purpose, MFRtot is estimated based on sensor information using the well-known speed-density method, and MFRegr is estimated based on EGR valve position and other engine parameters. This approach is typically very accurate under steady-state conditions, but is not valid, of course, under transient operating conditions. Furthermore, the steady-state estimate tends to be noisy during conditions of relatively high intake manifold pressure. Accordingly, the steady-state estimate is not continuously reliable over a range of different engine operating conditions.

The present invention provides a continuously reliable estimate of EGR concentration using a dynamic EGR model that is valid during both transient and steady state operating conditions of engine 10, and adjusting the estimated EGR concentration during steady-state operation of the engine based on a deviation of the dynamic EGR model from the above-described steady-state model. The dynamic EGR model is based on a first dynamic sub-model of mass flow and mixing of air and EGR in the intake manifold 46 and a second dynamic sub-model of transport delay in the intake runners 52 between intake manifold 46 and the combustion chamber intake ports 67.

The intake manifold sub-model comprehends four incoming gas flows: (1) the EGR mass flow rate MFRegr in conduit 84; (2) the throttle flow rate MFRthr past throttle plate 22; (3) the canister purge flow rate MFRpurge in conduit 38; and (4) the idle air control flow rate MFRiac in conduit 28. These flow rates are identified in FIG. 1 by arrows and corresponding legends. Additional mixing flows, if any, would be similarly comprehended.

In general, the mass of EGR gas in the intake manifold (Megr_im) is given by the product of the dynamic EGR concentration in the intake manifold (DYN%EGR_im) and the total mass of gas in the intake manifold (Mtot_im). That is:

$$Megr\_im = Mtot\_im * DYN\%EGR\_im \tag{2}$$

Differentiating Megr_im yields the differential equation:

$$d(Megr\_im)/dt = Mtot\_im[d(DYN\%EGR)/dt] + DYN\%EGR\_im[d(Mtot\_im)/dt] \tag{3}$$

Additionally, flow continuity considerations allow d(Megr_im)/dt and d(Mtot_im)/dt to be represented in terms of the imbalance of corresponding incoming and outgoing flows, as follows:

$$d(Megr\_im)/dt = (MFRegr\_in) - (MFRegr\_out), \text{ and} \tag{4}$$

$$d(Mtot\_im)/dt = (MFRtot\_in) - (MFRtot\_out) \tag{5}$$

Combining equations (3)–(5) yields an expression for d(DYN%EGR_im)/dt as follows:

$$d(DYN\%EGR\_im)/dt = (1/Mtot\_im)[MFRegr - (DYN\%EGR\_im * (MFRtot))] \tag{6}$$

where MFRegr_in is replaced by MFRegr since the only EGR flow into intake manifold 46 is the EGR valve flow in conduit 84. The coefficient (1/Mtot_im), referred to herein as intake manifold time constant TCim, may be given in the terms of the measured intake manifold pressure (MAP) and temperature (Tim), and its volume (Vim) as follows:

$$1/Mtot\_im = TCim = (Tim * R)/(MAP * Vim) \tag{7}$$

where R is a gas constant. Also, the term (MFRtot) is simply the sum of the various mass flow rates MFRegr, MFRthr, MFRpurge and MFRiac. Thus, equation (6) may be recast as follows:

$$d(DYN\%EGR\_im)/dt = [(Tim * R)/(MAP * Vim)] * [MFRegr - (DYN\%EGR\_im * (MFRegr + MFRthr + MFRpurge + MFRiac))] \tag{8}$$

The intake runner sub-model assumes bulk or plug motion of the intake manifold EGR/air gas mixture in the intake runners 52. Accordingly, the intake runner flow dynamics are described in terms of volume displacement, and the EGR concentration at the combustion chamber intake ports 67 (%EGR_ip) is simply a delayed version of the EGR concentration in the intake manifold 46 (DYN%EGR_im). The amount of delay (DELAY) is proportional to the ratio of the intake manifold runner volume (Vr) to the combustion chamber volume (Vcc), or Vr/Vcc. In the illustrated embodiment, DELAY is defined as:

$$DELAY = 2 * (Vr/Vcc) \tag{9}$$

where DELAY is given in terms of engine revolutions, and the factor two accounts for the fact that there are two engine revolutions per engine cycle in the four-stroke engine 10.

Although the steady-state solution of the above-described dynamic model is theoretically identical to the steady-state model given in equation (1) above, differences occur due to inaccurate estimates of the individual mass flow rate components MFRegr, MFRthr, MFRpurge, MFRiac and MFRtot. For this reason, the method of the present invention develops a corrected dynamic estimate of the EGR concentration for control purposes by closed-loop adjustment of the EGR concentration provided by the dynamic model, based on a deviation (ERROR) of the dynamic model from the steady-state model during steady-state operation of engine 10. Thus, ERROR is defined in terms of the dynamic and steady-state intake manifold EGR concentrations DYN%EGR_im and SS%EGR as follows:

$$ERROR = DYN\%EGR\_im - SS\%EGR_f \tag{10}$$

where $SS\%EGR_f$ is a low-pass filtered version of SS%EGR for improved noise immunity under high-MAP operating conditions. The ERROR is used to generate proportional and integral error terms that adjust the dynamic EGR concentration model of equation (8) as follows:

$$d(DYN\%EGR\_im)/dt = [d(DYN\%EGR\_im)/dt]_S + (Kp * ERROR) + [Ki * INT(ERROR)] \tag{11}$$

where $[d(DYN\%EGR\_im)/dt]_S$ is the EGR concentration computed according to equation (8), Kp and Ki are proportional and integral gains, respectively, and INT designates an integral function. Once the differential d(DYN%EGR_im)/dt has been computed, it is integrated to form the intake manifold EGR concentration DYN%EGR_im, and delayed according to equation (9) to determine the intake port EGR concentration %EGR_ip.

Finally, it is especially important in certain engine control applications to accurately estimate the concentration of inert EGR gas at the intake ports 67. This can be easily achieved with the above-described methodology if the fraction of inert gas in the recirculated exhaust gas is known or can be reliably estimated. This inert gas fraction, referred to herein as the Exhaust Inert Ratio or EIR, can be applied to the EGR mass flow rate (MFRegr) to yield the inert EGR mass flow rate MFRinert_egr. That is:

$$MFRinert\_egr=MFRegr*EIR \quad (12)$$

In this case, equations (1) and (8) discussed above are computed as follows:

$$SS\%EGR=MFRinert\_egr/MFRtot \quad (1a)$$

$$d(DYN\%EGR\_im)/dt=[(Tim*R)/(MAP*Vim)]*[MFRinert\_egr-(DYN\%EGR\_im*(MFRegr+MFRthr+MFRpurge+MFRiac))] \quad (8a)$$

The computed EGR concentration $d(DYN\%EGR\_im)/dt$ of equation (8a) will represent the concentration rate of inert EGR gas in the intake manifold, and the corresponding value of %EGR_ip will represent the concentration of inert EGR gas at the combustion chamber intake ports 67.

In a preferred embodiment of the present invention, the Exhaust Inert Ratio (EIR) is modeled in terms of the relative air fuel ratio RAFR and the estimated inert intake port EGR concentration %EGR_ip_inert, assuming perfect combustion efficiency and neglecting the effects of residual gases in the combustion chambers 54. Specifically, EIR is modeled as:

$$EIR=\%EGR\_ip\_inert\,[1-(1/RAFR)]+(1/RAFR) \quad (13)$$

where RAFR is defined as the engine air/fuel ratio (AFReng) relative to the stoichiometric air/fuel ratio AFRstoic, with AFReng being given in terms of MFRtot, %EGR_ip_inert and the engine fuel flow EFF as follows:

$$AFReng=MFRtot*(1-\%EGR\_ip\_inert)/EFF \quad (14)$$

Figure 2:
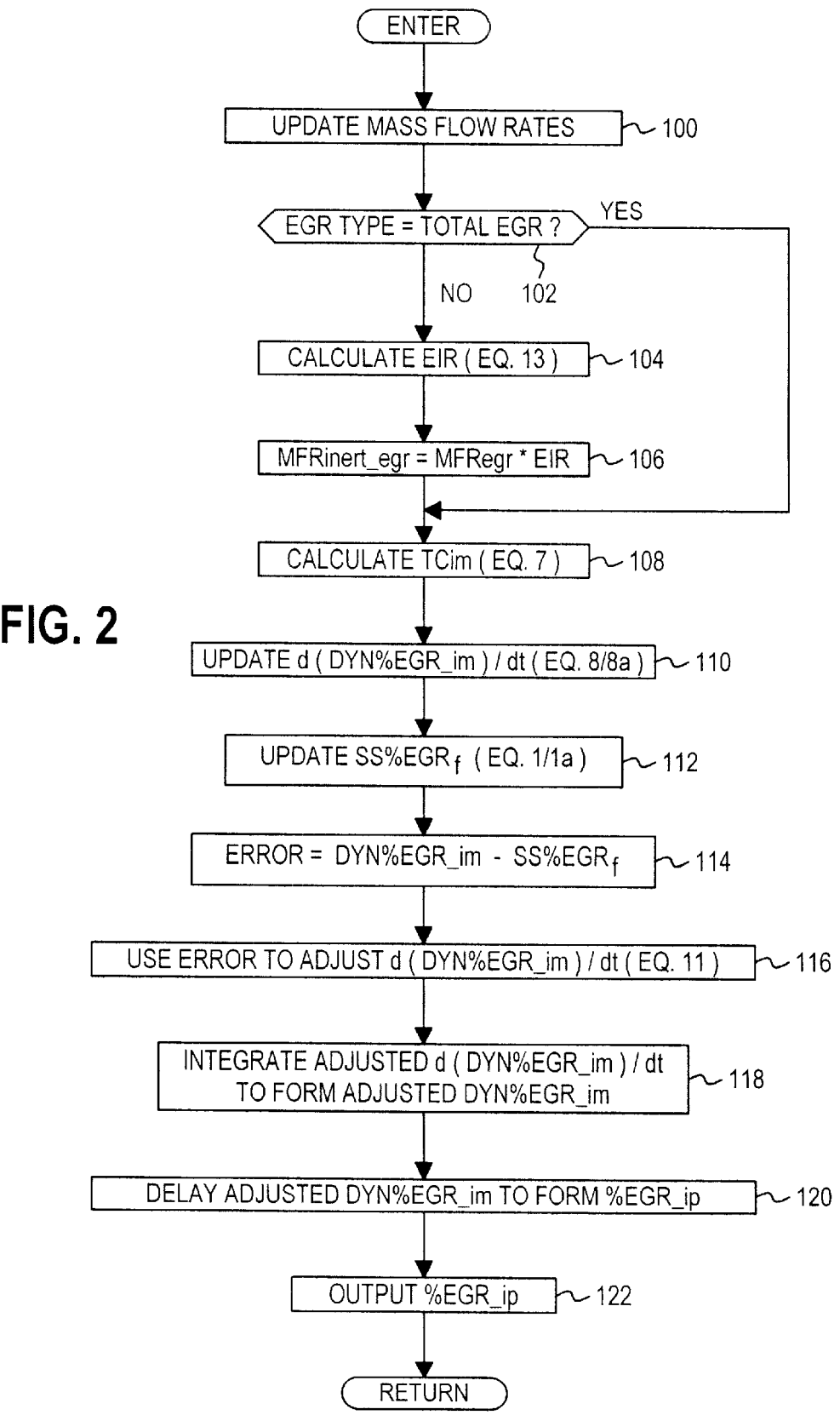
FIG. 2 is a flow diagram depicting the control method carried out by the engine control module of FIG. 1 according to this invention.

The flow diagram of FIG. 2 depicts an exemplary mechanization of the above-described method, and is a high-level description of a computer program routine that is periodically executed by ECM 12 of FIG. 1. As indicated at block 100, ECM 12 first updates its estimations of the above-mentioned mass flow rates, including MFRtot, MFRegr, MFRthr, MFRpurge and MFRiac. These mass flow rates may be determined by measurement and/or estimation, as described in detail for example, in the U.S. Patent to Olin et al. U.S. Pat. No. 5,845,627, issued on Dec. 8, 1998, and incorporated herein by reference. If an estimate of the inert EGR concentration is desired, as determined at block 102, the blocks 104 and 106 are executed to determine the Exhaust Inert Ratio EIR and to set the inert EGR mass flow rate MFRinert_egr equal to the product (MFR_egr*EIR). If an estimate of the total EGR concentration is desired, the blocks 104 and 106 are skipped, as indicated. The blocks 108 and 110 are then executed to update the dynamic model for the intake manifold EGR concentration rate; block 108 computes the intake manifold time constant TCim, and block 110 solves equation (8) for the total EGR case and equation (8a) for the inert EGR case. The block 112 updates the steady-state model for the intake manifold EGR concentration (SS%EGR) using equation (1) or (1a) and a conventional first-order low-pass filter function, and block 114 computes the deviation (ERROR) of dynamic model EGR concentration from the steady-state model EGR concentration. It will be noted that equations (8) and (8a) require knowledge of the previous value of DYN%EGR_im, and this value is also used to compute ERROR at block 114. Initially, DYN%EGR_im may be set equal to SS%EGR_im or a predetermined default value, as will be understood to those skilled in the art. Block 116 is then executed to sum the result of equation (8) with proportional and integral closed-loop terms based on ERROR, as defined in equation (11). Blocks 118 and 120 are then executed to integrate and delay the result of block 116 to form the intake port EGR concentration %EGR_ip, which is outputted at block 122. The integration step may be performed conventionally, as follows:

$$DYN\%EGR\_im=DYN\%EGR\_im_{old}+d(DYN\%EGR\_im)/dt \quad (15)$$

where the subscript "old" indicates the value of a term from the previous execution of the routine, and dt is the time step or execution rate of the routine.

As indicated above, the routine of FIG. 2 is generally configured to estimate either the inert intake port EGR concentration or the total intake port EGR concentration, either estimate being designated by the term %EGR_ip. That is, if the inert estimate is selected, blocks 104 solves equation (13) to compute EIR, blocks 110 and 112 solve equations (8a) and (1a), respectively, and the value of %EGR_ip computed at block 120 represents the inert intake port EGR concentration. However, if the total EGR concentration estimate is selected, an estimate of the inert EGR concentration %EGR_ip_inert may be determined by computing the exhaust inert ratio EIR in terms of the total EGR concentration estimate %EGR_ip_total, and multiplying the result by %EGR_ip_total. Specifically, the product (%EGR_ip_total*EIR) is substituted for %EGR_ip_inert in equation (13), and solving for EIR, yields:

$$EIR=(1/RAFR)/[1-(\%EGR\_ip\_total*(1-(1/RAFR))] \quad (16)$$

The inert EGR concentration %EGR_ip_inert may then be estimated according to the product (EIR*%EGR_ip_total).

In summary, the method of this invention provides an estimate of EGR concentration that is reliable during both steady-state and transient operating conditions. This, in turn, enables the more aggressive utilization of EGR for improved fuel efficiency and emission control, without causing combustion instability. While described in reference to the illustrated embodiment, it is expected that various modifications in addition to those mentioned above will * occur to those skilled in the art. For example, the method is applicable to different engine configurations than shown in FIG. 1; in this regard, the knowledge of the inert EGR concentration is particularly useful in connection with direct injection gasoline engines, as mentioned above. Additionally, the adjustment of the dynamic modeled EGR concentration may be selectively instead of continuously enabled, if desired. Thus, it will be understood that control methodologies incorporating these and other modifications may fall within the scope of this invention, which is defined by the appended claims.

What is claimed is:

1. A method of estimating a concentration of recirculated exhaust gas at an intake port of an internal combustion engine comprising the steps of:

estimating a first concentration of recirculated exhaust gas in an intake manifold plenum of said engine using a dynamic model of air and exhaust gas mixing in said intake manifold plenum based on air and exhaust gas flow estimates, and delaying said first concentration to form an estimate of said concentration of recirculated exhaust gas at said intake port;

estimating a second concentration of recirculated exhaust gas in said intake manifold plenum using a steady-state model of said concentration based on an estimate of exhaust gas flow into said intake manifold plenum and an estimate of total gas flow through said intake manifold plenum; and compensating said estimate of the concentration of recirculated exhaust gas at said intake port for error in said air and exhaust gas flow estimates by adjusting said first concentration based on a deviation of said first concentration from said second concentration.

2. The method of claim 1, wherein compensating said first concentration includes the step of:

adjusting said first concentration in relation to said deviation and in relation to an integral of said deviation.

3. The method of claim 1, wherein said dynamic model is based on said air and exhaust gas flow estimates, and a temperature, pressure and volume of gases in said intake manifold plenum.

4. The method of claim 1, including the steps of:

estimating an inert fraction corresponding to a concentration of inert gas in said recirculated exhaust gas; and estimating said first and second concentrations based on said inert fraction so that the delayed first concentration represents a concentration of inert recirculated exhaust gas at said intake port.

5. The method of claim 1, including the steps of:

estimating an inert fraction corresponding to a concentration of inert gas in said recirculated exhaust gas; and estimating a concentration of inert recirculated exhaust gas at said intake port according to a product of said delayed first concentration and said inert fraction.

6. The method of claims 4 or 5, wherein said inert fraction is estimated based on an estimated air/fuel ratio of the engine relative a stoichiometric air/fuel ratio.

7. A method of estimating a concentration of recirculated exhaust gas entering a combustion chamber of an internal combustion engine comprising the steps of:

estimating a dynamic concentration of recirculated exhaust gas in an intake manifold plenum of the engine using a dynamic model of air and exhaust gas mixing based on air and exhaust gas flow estimates, a volume of said intake manifold plenum, and a measured pressure and temperature of gases in said intake manifold plenum;

estimating a steady-state concentration of recirculated exhaust gas in said intake manifold plenum using a steady-state model based on an estimate of exhaust gas flow into said intake manifold plenum and an estimate of total gas flow entering said combustion chamber;

adjusting said dynamic concentration based on a deviation of said dynamic concentration from said steady-state concentration, thereby to compensate said dynamic concentration for error in said air and exhaust gas flow estimates;

integrating the adjusted dynamic concentration to form an estimate of the recirculated exhaust gas concentration in said intake manifold plenum; and delaying the estimate of the recirculated exhaust gas concentration in said intake manifold plenum to form an estimate of the recirculated exhaust gas concentration entering said combustion chamber.

8. The method of claim 7, wherein adjusting said dynamic concentration includes the step of:

adjusting said dynamic concentration in relation to said deviation and in relation to an integral of said deviation.

9. The method of claim 7, wherein gases in said intake manifold plenum pass through an intake runner to said combustion chamber, and the estimate of the recirculated exhaust gas concentration in said intake manifold plenum is delayed in proportion to a ratio of a volume of said intake runner to a volume of said combustion chamber.

10. The method of claim 7, including the steps of:

estimating an inert fraction corresponding to a concentration of inert gas in said recirculated exhaust gas; and estimating said dynamic and steady-state concentrations based on said inert fraction so that said delayed estimate represents a concentration of inert recirculated exhaust gas entering said combustion chamber.

11. The method of claim 7, including the steps of:

estimating an inert fraction corresponding to a concentration of inert gas in said recirculated exhaust gas; and estimating a concentration of inert recirculated exhaust gas entering said combustion chamber according to a product of said estimate of the recirculated exhaust gas concentration entering said combustion chamber and said inert fraction.

12. The method of claims 10 or 11, wherein said inert fraction is estimated based on an estimated air/fuel ratio of the engine relative a stoichiometric air/fuel ratio.

* * * * *